United States Patent
Lob et al.

[11] Patent Number: 5,888,206
[45] Date of Patent: Mar. 30, 1999

[54] JOINT PROTHESIS

[75] Inventors: Günter Lob, München; Hans-Joachim Fischer, Berlin; Gerd Steür, Berlin; Curt Kranz, Berlin, all of Germany

[73] Assignee: Merck Patent GmbH, Darmstadt, Germany

[21] Appl. No.: 836,706

[22] PCT Filed: Nov. 20, 1995

[86] PCT No.: PCT/DE95/01642

§ 371 Date: Aug. 6, 1997

§ 102(e) Date: Aug. 6, 1997

[87] PCT Pub. No.: WO96/15737

PCT Pub. Date: May 30, 1996

[30] Foreign Application Priority Data

Nov. 19, 1994 [DE] Germany ............... 44 42 206.7

[51] Int. Cl.⁶ .......................................... A61F 2/36
[52] U.S. Cl. .............................................. 623/23
[58] Field of Search ............................ 623/23, 22

[56] References Cited

U.S. PATENT DOCUMENTS

| 3,683,421 | 8/1972 | Martinie | 623/23 |
| 4,693,724 | 9/1987 | Rhenter | 623/23 |
| 4,795,473 | 1/1989 | Grimes | 623/23 |
| 5,507,830 | 4/1996 | DeMane | 623/23 |
| 5,591,233 | 1/1997 | Kelman | 623/23 |

FOREIGN PATENT DOCUMENTS

| 0010527 | 4/1980 | European Pat. Off. . |
| 0399920 | 11/1990 | European Pat. Off. . |
| 0586824 | 3/1994 | European Pat. Off. . |
| 1099519 | 9/1955 | France . |
| 2183230 | 12/1973 | France . |
| 2575383 | 7/1986 | France . |
| 2629707 | 10/1989 | France . |
| 2639820 | 6/1990 | France . |
| 2651118 | 3/1991 | France . |
| 2674119 | 9/1992 | France . |
| 2854334 | 6/1980 | Germany . |
| 8701164 U | 7/1987 | Germany . |
| 9418963 U | 3/1995 | Germany . |
| 85/05027 | 11/1985 | WIPO . |

*Primary Examiner*—Michael J. Milano
*Attorney, Agent, or Firm*—Venable; Robert Kinberg

[57] ABSTRACT

A joint prosthesis includes a shaft part insertable into a tubular bone and a head part joining the shaft part and including a joint connection element. The head part includes a sleeve region having a through bore adapted to a cross section of a shaft of the joint connection element. The longitudinal axis of the shaft part and the joint connection element form an obtuse angle when the joint connection element is introduced into the through bore of the head part.

28 Claims, 4 Drawing Sheets

JOINT PROTHESIS

BACKGROUND OF THE INVENTION

The invention relates to a modular joint prosthesis having a shaft part insertable into a tubular bone and a head part, adjoining the shaft part, and having a joint connection element, the longitudinal axes of the shaft part and joint connection element forming an obtuse angle.

Shaft prostheses of this kind are produced in various shapes and sizes, to assure that the needs of a given patient can be optimally met.

International Patent Application WO 85/05027 discloses an artificial joint system, in particular a hip joint prosthesis for cementless implantation, which has a shaft part that can be introduced into the upper thigh of the patient and a joint connection element connected to this shaft part. In the proximal region of the shaft part, a threaded sleeve is provided, into which the joint connection element is screwed; the longitudinal axis of the shaft part and the longitudinal axis of the joint connection element are inclined relative to one another. Accordingly, the joint connection element has a threaded peg, which on its proximal end is connected to a conical shaft part for receiving the ball of the joint. The process of screwing the prosthesis in is concluded once the conical shaft part of the joint connection element rests firmly on the proximal region, prepared for the implantation, of the upper thigh bone.

However, the above-described version has the disadvantage that only a complete replacement of the joint, including the ball of the joint, can be done with it.

SUMMARY OF THE INVENTION

Given the deficiencies of the prior art, it is the object of the invention to create a modular hip prosthesis shaft of the generic type described at the outset, whose structural design makes it simple even to replace component elements in the region of the joint, to allow adaptation to variously advanced stages of disease.

The above and other objects are accomplished according to the invention by the provision of a joint prosthesis, comprising: a shaft part insertable into a tubular bone and having a first longitudinal axis; a head part adjoining the shaft part and including a sleeve region which has a through bore that has a second longitudinal axis which forms an obtuse angle with the first longitudinal axis; and a joint connection element having a shaft for being received in the through bore of the head part, the through bore of the head part being adapted to a cross section of the shaft of the joint connection element, the joint connection element having a third longitudinal axis forming essentially the same obtuse angle with the first longitudinal axis that the second longitudinal axis makes with the first longitudinal axis when the joint connection element is introduced in the through bore, the shaft of the joint connection element including a cylindrical region that is expandable by a spreader device to lock the joint connection element in place in the through bore of the head part.

The invention encompasses the recognition that to preserve the natural ball of the joint in a modular prosthesis, one additional, alternatively usable head part is favorable that is provided with a bone screw in the direction of the neck of the ball of the joint that can be screwed into the separate, natural ball of the joint. Thus the joint with its natural parts, the ball and socket of the joint, may possibly be preserved for a still longer time. The head part can then later be replaced if needed, at little effort, without stressing the bone substance of the patient and without loosening and removing the prosthesis seat.

With the provisions of the invention, the prosthesis described can initially also replace a conventional hip screw, of the kind that is often inserted in the region of the femur in the event of fractures. Later reoperation is then facilitated in the sense that to obtain a full prosthesis, only the head part of the modular shaft prosthesis needs to be replaced with a head part that has an artificial ball for the joint.

The modular hip prosthesis shafts according to the invention have individual elements embodied as the joint connection element and the shaft part, which are joined together preferably by putting together their proximal and distal ends, respectively. The joint connection element serves to make a secure connection between the prosthesis shaft and the hip joint.

Because of the modular nature of the prosthesis, when the modular hip joint shaft is adapted to given anatomical conditions, the joint connection element can be changed in its position even without exerting particular force and subsequently securely fastened again in a simple way.

While preserving the natural head of the joint, it is advantageously possible with the provisions of the invention to correct the position of the joint connection element in order to adapt to the particular anatomical conditions of the patient (for instance, a relatively slight axial displacement in the neck direction) during the implantation process.

It is also advantageous that in the prosthesis of the invention, the connections of the modular elements with one another can also be undone with little effort in a reoperation even after having been implanted for some time, should that become necessary from a medical standpoint, for instance for replacement or readjustment of the joint connection element. Conventional connections, conversely, often stick together so firmly that if disassembly becomes necessary, damage to the upper thigh bone or at least undesired loosening of the end part is often unavoidable, to the detriment of the patient.

In a preferred embodiment of the invention, the joint connection element is embodied as a bone screw that is insertable into a through channel disposed on the proximal end of the shaft part on an incline to the longitudinal axis of the shaft part and can be fixed there in various positions by retaining means. In this way, in addition to variability because of the modular construction of the shaft, including the neck region, it is also possible to make a finely tuned adaptation to individual conditions of the patient.

The retaining means are embodied as spreading means for wedging purposes, in such a way that they enable a radial expansion of the cross section of the portion of the joint connection element thrust into the shaft part, and are thus activatable without exerting particular force.

In accordance with another favorable further feature of the invention, a cylindrical region is provided as the through channel. The region of the shaft of the joint connection element thrust into the through bore takes the form of a sleeve slit in the direction of the longitudinal axis, so that by screwing in a conical threaded bolt, spreading of the sleeve is attainable, thus creating a secure positive and nonpositive connection between the shaft part and the joint connection element.

By reducing the spreading, the connection between the shaft part and the joint connection element is favorably loosenable, thus enabling replacement or positional correction of the joint connection element. This assures simplified adaptation of the joint prosthesis to existing anatomical conditions of a specific patient. If replacement of the fastener later becomes necessary, this can be done without particular mechanical strain on the shaft part, located in the upper thigh bone, of the hip prosthesis shaft, something that in the least favorable case can cause irreversible loosening of the shaft part.

In an advantageous embodiment of the invention, the joint connection element is embodied as a bone screw, which is used whenever the femur is damaged but the natural ball of the joint is worth preserving.

If the damage to the ball of the joint becomes more extensive, then in a further feature of the invention, instead of the bone screw a ball head with a leg is used as the joint connection element, the free end of the peg being embodied as a slit sleeve. This replacement of the bone screw, in which the ball head is inserted into the existing hip joint socket, is accomplished with minimal mechanical stress on the already-implanted shaft part threatening its seating.

In another further feature of the invention, the shaft part can be divided into a head part that carries the artificial ball of the joint and a neck part, the two component elements being joined together by means of a conical insert connection.

Corresponding conical insert connections are also used with the component elements of the modularly put-together shaft. This shaft can be secured or set in the longitudinal direction by a tie rod or a screw connection, which—being guided through an additional axial channel in the head part—can be screwed into a threaded bore, located on the same axis, in the end part of the shaft.

To be able, for the sake of further simplification of adapting an already-implanted prosthesis to altered anatomical conditions of the patient, to undertake a division of the head part, carrying the joint connection element, from the end part located in the upper thigh bone without subjecting the end part to an additional mechanical stress that would impair the firm seat of the implant, according to a favorable further feature of the invention. The cylindrical channel in the head part of the modular joint prosthesis is embodied as a threaded bore. The diameter of this threaded bore is greater than the diameter of the threaded bore in the end part that receives the tie rod.

A diameter ratio in the range from 1.5 to 2.5 assures that on the proximal, frustoconical end of the end part, a substantially circular-annular portion of the top face of the truncated cone is available as an abutment for a screw bolt, which can be screwed into the head part once the tie rod has been removed. The bolt screwed into the head part is braced on the substantially circular-annular abutment, and upon a further screwing motion, an axial pressure force is favorably generated, which releases the firm conical insert connection (despite the absence of the tie rod) between the head part and the end part enough that the head part can be removed for replacement purposes, or can be swiveled to the desired extent with regard to the end part on its frustoconical peg provided on the proximal end.

In another advantageous further feature of the invention, the thread provided for the screw bolt extends in the head part of the modular joint prosthesis over the entire length of the available cylindrical channel. For both the threaded bore in the head part of the hip prosthesis shaft and for the threaded portion on the proximal end of the end part, a metric thread is provided. The thread in the head part has a lesser pitch than the thread on the proximal end of the end part and thereby makes it easier to generate the pressure force, by means of the screw bolt, that is required to loosen the firm conical insert connection.

In another further feature of the invention, the proximal end of the threaded bore provided in the end part has a recess, which is favorably embodied as a chamfer disposed symmetrically to the longitudinal axis of the bore. As a result, it is advantageously attained that the screw bolt, which is used to loosen the conical insert connection and whose free end is likewise embodied with a chamfer at the same angle, cannot enter into operative contact, when braced on the proximal end of the end part, with the thread of the threaded bore provided in this region. As a result, when the pressure force required to loosen the conical insert connection between the head part and the shaft part is generated, deformation of the first few courses of the thread is averted. A deformed thread would make it impossible to screw the tie rod back into the proximal end of the end part after adaptation or replacement of the head part.

BRIEF DESCRIPTION OF DRAWINGS

Other advantageous further features of the invention will become apparent from the following detailed description of the invention, when considered in conjunction with the drawings. Shown are.

DETAILED DESCRIPTION OF THE INVENTION

Figure 1:
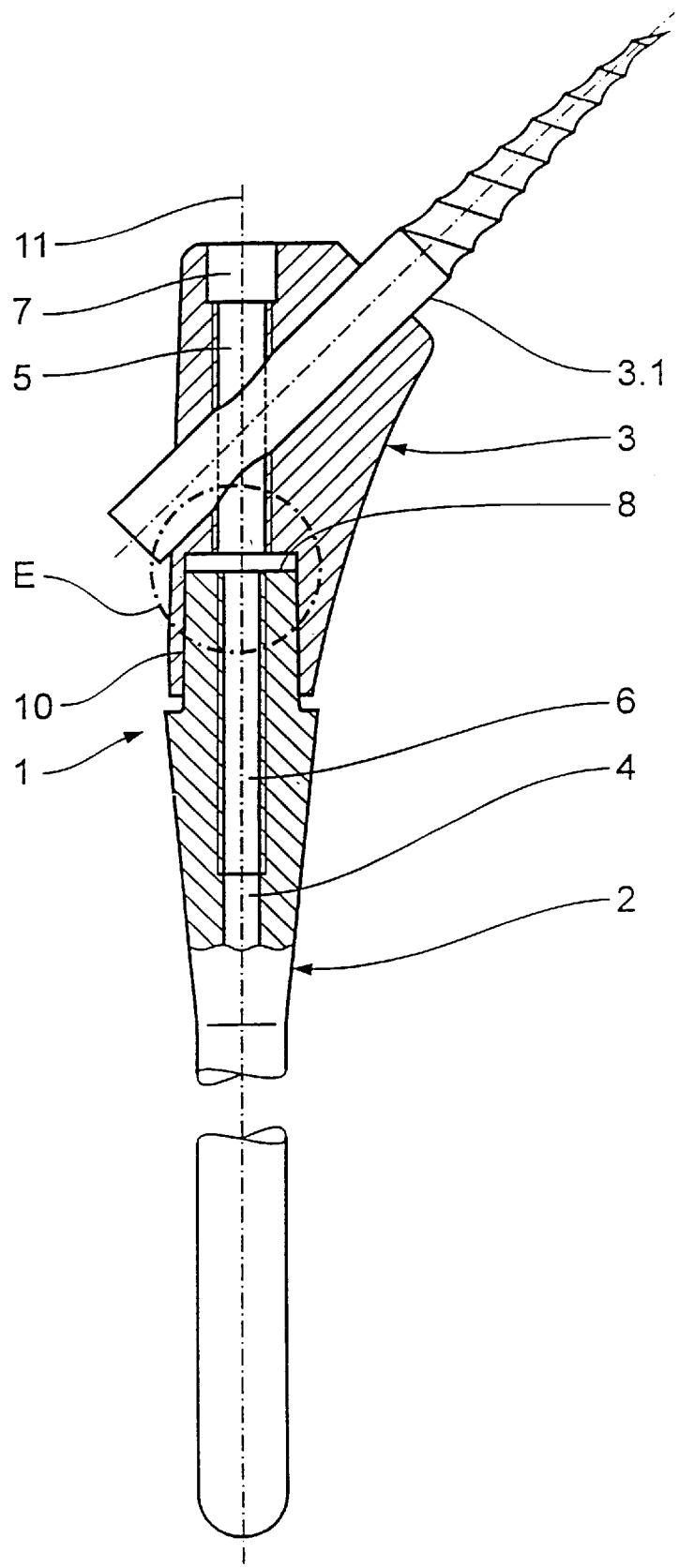
FIG. 1, a fragmentary longitudinal section through a preferred embodiment of the invention.

The modular joint prosthesis 1 shown in FIG. 1 comprises a shaft part 2 and a head part 3, each of which have profiling in the longitudinal direction. The head part 3 carries the joint connection element 3.1, embodied as a bone screw, by means of which the connection of the joint prosthesis 1 to the hip joint can be made. The longitudinal axes of the joint connection element 3.1 and the prosthesis shaft 1 form an angle of approximately 135°. The connection between the head part 3 and the joint connection element 3.1 is effected both positively and nonpositively.

The component elements 2 and 3 of the shaft 1 are joined together, located on the same axis and pivotable relative to one another, by means of a conical insert connection 10. For securing this insert connection against axial loosening, a tie rod (not shown) is provided, which is passed through the channel 5, embodied as a threaded bore, of the head part 3 and screwed into the proximal region 6, embodied as a threaded bore, of the channel 4 provided in the end shaft part 2. The screw insertion proceeds far enough that the proximal end of the tie rod is braced in the recess 7, and the individual parts 2 and 3 of the modular joint prosthesis 1 are moved axially toward one another, until the conical insert connection 10 has the desired strength.

In order to be able to vary the position of the head part 3, which has a joint connection element 3.1, relative to the end part 2 by pivoting it, or to replace the head part 3, the conical insert connection 10 must be loosened again. After the tie rod, (not shown) is loosened and removed by twisting, a screw bolt (also not shown) is screwed into the threaded bore 5 of the head part 3. Since the diameter $D_1$ of the threaded bore 5 in the head part 3 has a greater value than the diameter $D_2$ of the proximal portion 6 (see FIG. 4), provided with a thread, of the central bore 4 of the end part 2, the screw bolt is based against a circular ring, whose area is defined by the difference in diameter $D_1-D_2$, on the top face 8 of the proximal end, embodied as a truncated cone, of the head part 3 and is thus capable of generating an axially oriented pressure force. This force releases the insert connection 10, which is very firm because of the action of the tie rod, and conveniently makes it possible to readapt the joint prosthesis 1 to a patient's altered physical conditions.

In this connection, it has proved favorable for the manipulability of the means for generating the pressure force required to loosen the conical insert connection to provide a diameter ratio of the bores 4, 5 in the range from 1.5 to 2.5, and to provide the bore 5 with a thread over its entire length. Metric threads are used; the thread of the threaded bore 5 in the head part 3 has a lesser pitch than the thread in the proximal portion 6 of the bore 4 of the end part 2.

Figure 2:
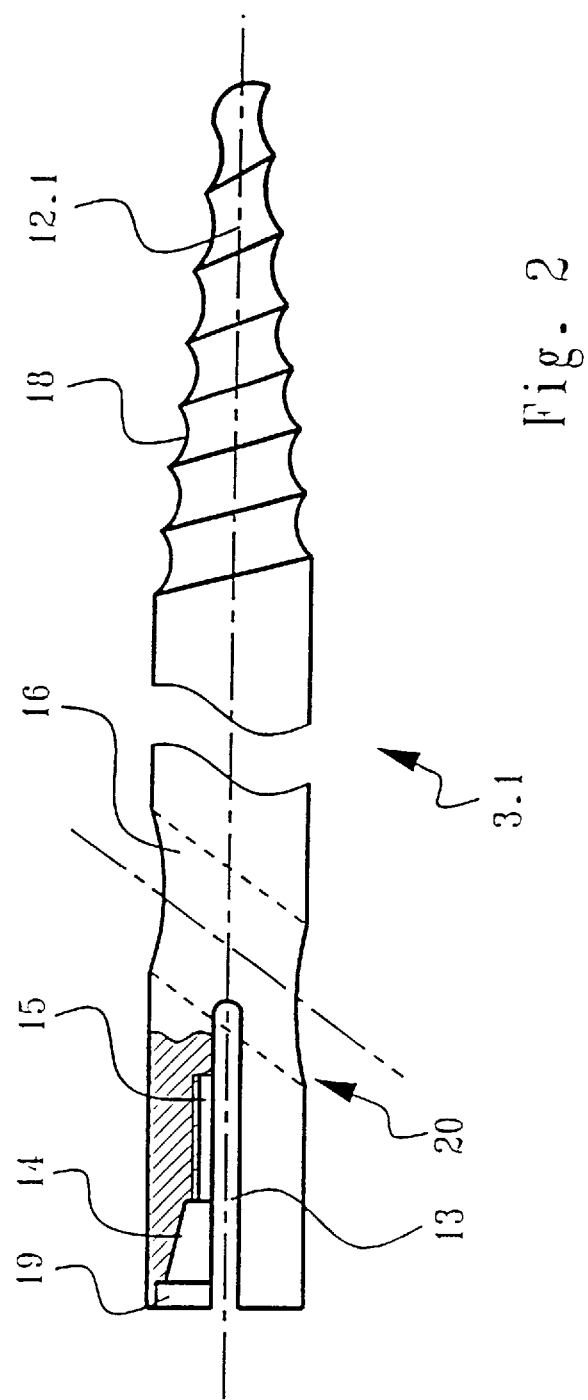
FIG. 2, the schematic illustration of a fastener, shown in FIG. 1, in a side view and fragmentary longitudinal section.
Figure 3:
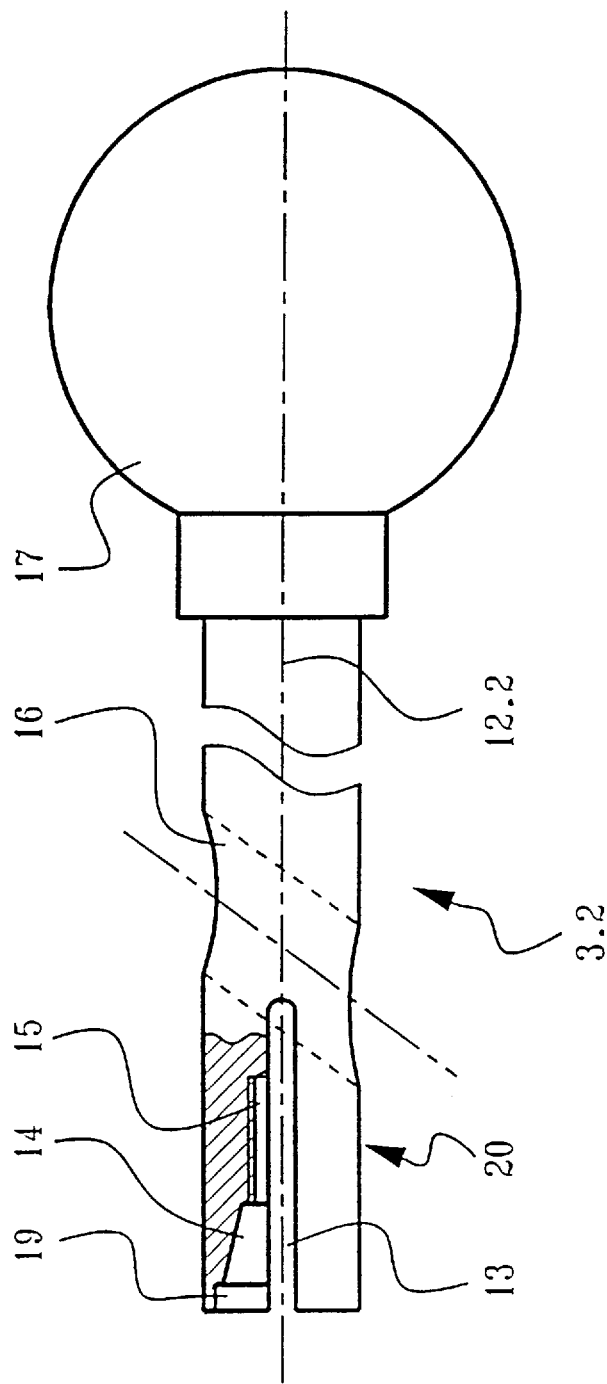
FIG. 3, a favorable further feature of the fastener, shown in FIG. 1, in a side view and fragmentary longitudinal section.

In FIGS. 2 and 3, advantageous embodiments of joint connection elements 3.1, 3.2 are shown schematically in fragmentary section. Both the sleevelike end of the bone screw 3.1 remote from the thread 18 and the cylindrical hollow peg of the joint connection element 3.2, which has a ball head 17, are provided with a slit 13. The walls of the slit 13 are spreadable by means of a bolt, which is based—being screwed into the threaded bore 15—on the wall of the conical recess 14, resulting in an increase in diameter, thus assuring a firm seat of the joint connection element in the head part 3. The bore 16, disposed in inclined fashion with respect to the longitudinal axes 12.1 and 12.2 of the joint connection elements 3.1 and 3.2, makes it possible to manipulate the tie rod (not shown) or the screw bolt (not shown) in order to connect or separate the individual parts 2 and 3 of the modular joint prosthesis 1.

Figure 4:
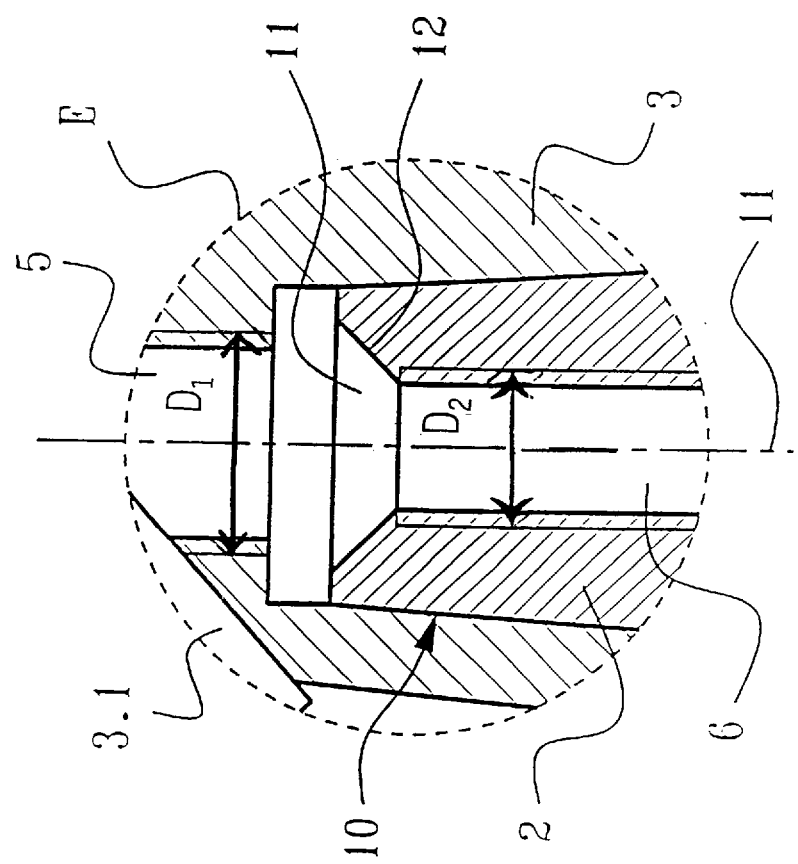
FIG. 4, detail E of FIG. 1, on a larger scale.

The detail E of FIG. 1, shown on a larger scale in FIG. 4, illustrates an advantageous further feature of the invention. To prevent an effective intervention of the screw bolt (not shown) on the top side of the proximal end of the end part 2 from damaging the threaded portion 6 provided there, a recess 11 embodied as a chamfer is provided on the proximal end of the threaded bore. The inclination of the flanks 12 amounts to 45° and corresponds to the inclination of the flanks of the chamfer on the threaded end of the screw bolt (not shown). As a result, an optimal introduction of force into the end part 2 can be accomplished, in order to enable loosening the conical insert connection 10 between the succeeding shaft part 3 and head part 2 with a relatively slight exertion of force. Damage to the thread of the bore portion 6 would make it impossible to refasten the head part and axially secure the conical insert connection by means of the tie rod.

It will be appreciated that—in further embodiments not shown in the drawing—by means of the attained modularity in a system of shaft prostheses for attaining different individually dimensioned prosthesis forms, various sizes of elements can be combined with one another. The graduation in thread diameters provided according to the invention can likewise be provided between different successive elements. Thus it is possible to achieve a division—if desired—not only between the head part and the distally succeeding shaft part but also between different shaft parts, for instance. For purposefully "dialing up" a connection that is to be released, with thread diameters that increase in stages toward the head end, one would then have to look for a bolt whose male thread comes into engagement with the female thread, which comes into engagement with the shaft element located on the proximal side of the intended dividing point. It is then braced by the edge of its end on the edge of the bore of the distally adjacent element and separates the selected connection.

In a modular system with differently curved shaft elements, individually shaped shafts can be created by means of different relative angle positioning, without in any way limiting the releasability of the connection as described above.

The invention is not limited in its realization to the preferred exemplary embodiment described above. On the contrary, a number of variants are conceivable, which make use of the provisions described, even in fundamentally different types of embodiments.

We claim:

1. A joint prosthesis, comprising:
   a shaft part insertable into a tubular bone and having a first longitudinal axis;
   a head part adjoining the shaft part and including a sleeve region which has a through bore that has a second longitudinal axis which forms an obtuse angle with the first longitudinal axis; and
   a joint connection element having a shaft for being received in the through bore of the head part, the through bore of the head part being adapted to a cross section of the shaft of the joint connection element, the joint connection element having a third longitudinal axis forming essentially the same obtuse angle with the first longitudinal axis that the second longitudinal axis makes with the first longitudinal axis when the joint connection element is introduced in the through bore, the shaft of the joint connection element including a cylindrical region that is expandable by a spreader device to lock the joint connection element in place in the through bore of the head part.

2. The joint prosthesis of claim 1, wherein the joint connection element is supported longitudinally displaceably and lockably in the sleeve region.

3. The joint prosthesis of claim 1, wherein the joint connection element comprises one of a bone screw having a thread-free cylindrical region and an artificial ball of a joint having a thread-free cylindrical region.

4. The joint prosthesis of claim 1, wherein the cylindrical region comprises, at least in part, a spreadable sleeve including a longitudinally extending slit defining opposing slit walls.

5. The joint prosthesis of claim 4, wherein the spreader device comprises a screw bolt with a region that tapers toward its shaft end for spreading the slit walls of the joint connection element.

6. The joint prosthesis of claim 1, further comprising a conical insert connection joining the head part with the shaft part.

7. A kit for making the joint prosthesis of claim 1, comprising, a selection of head parts of different length and/or different diameter and a selection of shaft parts of different length, different diameter and/or different curvature.

8. The kit of claim 7, wherein the head parts have a diameter in a range from 12 to 17 mm and the shaft parts have a length range from 200 to 320 mm and a diameter range from 10 to 14 mm.

9. The prosthesis of claim 1, wherein the head part and the shaft part are separate parts and further including a connecting means connecting the head part and the shaft part in a manner to permit the head part to pivot relative to the shaft part.

10. A joint prosthesis, comprising:

a shaft part insertable into a tubular bone and having a first longitudinal axis;

a head part adjoining the shaft part, the head part including an axial bore extending in the direction of the first longitudinal axis and a sleeve region which has a through bore that has a second longitudinal axis which forms an obtuse angle with the first longitudinal axis; and a joint connection element having a shaft for being received in the through bore of the head part, the through bore of the head part being adapted to a cross section of the shaft of the joint connection element, the joint connection element having a third longitudinal axis forming essentially the same obtuse angle with the first longitudinal axis that the second longitudinal axis makes with the first longitudinal axis when the joint connection element is introduced in the through bore, wherein the joint connection element has a through bore that constitutes a continuation of the axial bore of the head part when the joint connection element is longitudinally supported in the head part.

11. The joint prosthesis of claim 10, wherein the joint connection element is supported longitudinally displaceably and lockably in the sleeve region.

12. The joint prosthesis of claim 10, wherein the joint connection element comprises one of a bone screw having a thread-free cylindrical region and an artificial ball of a joint having a thread-free cylindrical region.

13. The joint prosthesis of claim 10, wherein the shaft of the joint connection element includes a cylindrical region that is expandable by a spreader device to lock the joint connection element in place in the through bore of the head part and the cylindrical region comprises, at least in part, a spreadable sleeve including a longitudinally extending slit defining opposing slit walls.

14. The joint prosthesis of claim 13, wherein the spreader device comprises a screw bolt with a region that tapers toward its shaft end for spreading the slit walls of the joint connection element.

15. The joint prosthesis of claim 10, further comprising a conical insert connection joining the head part with the shaft part.

16. A kit for making the joint prosthesis of claim 10, comprising a selection of head parts of different length and/or different diameter and a selection of shaft parts of different length, different diameter and/or different curvature.

17. The kit of claim 16, wherein the head parts have a diameter in a range from 12 to 17 mm and the shaft parts have a length range from 200 to 320 mm and a diameter range from 10 to 14 mm.

18. A joint prosthesis, comprising:

a shaft part insertable into a tubular bone and having an axial bore and a first longitudinal axis;

a head part adjoining the shaft part, the head part including an axial bore extending in the direction of the first longitudinal axis and a sleeve region which has a through bore that has a second longitudinal axis which forms an obtuse angle with the first longitudinal axis; and a joint connection element having a shaft for being received in the through bore of the head part, the through bore of the head part being adapted to a cross section of the shaft of the joint connection element, the joint connection element having a third longitudinal axis forming essentially the same obtuse angle with the first longitudinal axis that the second longitudinal axis makes with the first longitudinal axis when the joint connection element is introduced in the through bore;

wherein the axial bore of the shaft part has a proximal region adjacent the head part with a first diameter and a thread provided only in the proximal region, and the axial bore of the head part has a thread and a second diameter that is greater than the first diameter of the bore of the shaft part for loosening the head part and shaft part relative to one another when a screw is received in the axial bore of the head part.

19. The joint prosthesis of claim 18, wherein the thread in the axial bore in the head part extends over an entire length of the axial bore in the head part.

20. The joint prosthesis of claim 18, wherein the threaded bore of the shaft part has a proximal end adjacent the head part that has a chamfer.

21. The joint prosthesis of claim 18, wherein the joint connection element is supported longitudinally displaceably and lockably in the sleeve region.

22. The joint prosthesis of claim 18, wherein the joint connection element comprises one of a bone screw having a thread-free cylindrical region and an artificial ball of a joint having a thread-free cylindrical region.

23. The joint prosthesis of claim 18, wherein the shaft of the joint connection element includes a cylindrical region that is expandable by a spreader device to lock the joint connection element in place in the through bore of the head part and the cylindrical region comprises, at least in part, a spreadable sleeve including a longitudinally extending slit defining opposing slit walls.

24. The joint prosthesis of claim 23, wherein the spreader device comprises a screw bolt with a region that tapers toward its shaft end for spreading the slit walls of the joint connection element.

25. The joint prosthesis of claim 18, further comprising a conical insert connection joining the head part with the shaft part.

26. A kit for making the joint prosthesis of claim 18, comprising a selection of head parts of different length and/or different diameter and a selection of shaft parts of different length, different diameter and/or different curvature.

27. The kit of claim 26, wherein the head parts have a diameter in a range from 12 to 17 mm and the shaft parts have a length range from 200 to 320 mm and a diameter range from 10 to 14 mm.

28. The prosthesis of claim 18, wherein the thread in the axial bore of the head part has a lesser pitch than the pitch of the thread in the axial bore in the shaft part.

* * * * *